(12) United States Patent
Walker et al.

(10) Patent No.: US 12,135,174 B2
(45) Date of Patent: Nov. 5, 2024

(54) HEAT EXCHANGE SYSTEM FOR SURGICAL INSTRUMENT

(71) Applicant: Medical Instrument Development Laboratories, Inc., San Leandro, CA (US)

(72) Inventors: Jeffrey A. Walker, Livermore, CA (US); Erik W. Peterson, Walnut Creek, CA (US); David Chen, Fremont, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 938 days.

(21) Appl. No.: 17/174,486

(22) Filed: Feb. 12, 2021

(65) Prior Publication Data

US 2021/0247154 A1 Aug. 12, 2021

Related U.S. Application Data (60) Provisional application No. 62/975,471, filed on Feb. 12, 2020.

(51) Int. Cl.
| | |
|---|---|
| *F28F 25/12* | (2006.01) |
| *F28D 1/047* | (2006.01) |
| *A61B 17/00* | (2006.01) |
| *A61F 9/007* | (2006.01) |
| *F28D 21/00* | (2006.01) |

(52) U.S. Cl.
CPC ............ *F28F 25/12* (2013.01); *F28D 1/0472* (2013.01); *A61B 2017/00544* (2013.01); *A61F 9/00736* (2013.01); *A61F 9/00754* (2013.01); *F04C 2210/22* (2013.01); *F28D 2021/005* (2013.01); *F28F 2210/04* (2013.01)

(58) Field of Classification Search
CPC .......... A61F 9/00763; A61B 17/31002; A61B 2017/00544; F28F 21/08; F28F 25/12; F28F 21/081
See application file for complete search history.

(56) References Cited

U.S. PATENT DOCUMENTS

| | | | | |
|---|---|---|---|---|
| 2,755,639 A | * | 7/1956 | Straznicky | ........... B60H 1/3202 62/7 |
| 3,447,334 A | | 6/1969 | Kimball | |

(Continued)

FOREIGN PATENT DOCUMENTS

JP        4021141 B2    12/2007

OTHER PUBLICATIONS

European Patent Office Extended European Search Report for Application No. 21754034.3, dated Feb. 7, 2024 (7 pages).

(Continued)

*Primary Examiner* — Vi X Nguyen
(74) *Attorney, Agent, or Firm* — Michael Best & Friedrich LLP (57) ABSTRACT

A heat exchange system for a surgical instrument includes a valve, a load, and a load conduit extending between the valve and the load. The load conduit delivers fluid from the valve to the load. The heat exchange system also includes an exhaust conduit that directs the fluid away from the valve. A portion of the load conduit is positioned so as to thermally transfer heat to a portion of the exhaust conduit.

14 Claims, 5 Drawing Sheets

(56) References Cited

U.S. PATENT DOCUMENTS

| | | | |
|---|---|---|---|
| 3,894,349 A | 7/1975 | Moreau | |
| 4,381,649 A | 5/1983 | Franklin | |
| 4,870,828 A | 10/1989 | Hidaka | |
| 6,086,598 A | 7/2000 | Appelbaum et al. | |
| 6,383,203 B1 * | 5/2002 | Makihara | A61F 9/00763 606/171 |
| 6,575,550 B1 | 6/2003 | Steinfield | |
| 2012/0310146 A1 | 12/2012 | Easley | |
| 2014/0171991 A1 | 6/2014 | Lee et al. | |
| 2020/0340600 A1 | 10/2020 | Zhou et al. | |

OTHER PUBLICATIONS

International Search Report and Written Opinion for Application No. PCT/US2021/017814 dated Apr. 22, 2021 (10 pages).

* cited by examiner

HEAT EXCHANGE SYSTEM FOR SURGICAL INSTRUMENT

CROSS-REFERENCE TO RELATED APPLICATIONS

This application claims priority to U.S. Provisional Application No. 62/975,471, filed Feb. 12, 2020, the entire contents of which are incorporated herein by reference.

BACKGROUND

Surgical instruments, including pneumatically powered tools, are employed in many applications such as ophthalmic surgery. One method commonly used to operate a reciprocating mechanism in a pneumatically powered tool includes using a valve to alternately connect the reciprocating mechanism (load) of the tool to a source of compressed gas (pressure) and a lower pressure sink (exhaust). Such a valve can have one of several structures, including poppet, sliding and rotating.

When the pressure of a gas (e.g., compressed gas) is suddenly increased, its temperature increases. When the pressure is suddenly decreased, the temperature decreases. In the pneumatic systems described above, these effects cause the gas in a conduit connecting the valve to the load to have a higher temperature than the gas supplied at a pressure port of the valve, and the gas leaving the valve at an exhaust port to have a lower temperature. These effects are small when the cycling rate is slow enough to allow heat to be conducted away. At high cycle rates, however, these effects can be pronounced. Some vitreous cutting instruments used in ophthalmic surgery, for example, cyclically supply compressed air to the load within the instrument to generate the reciprocating action of the cutter, and then exhaust the air. In these vitreous cutting instruments, a high cycle rate (e.g., 200 cycles per second or more) of compressed air is typically found to be beneficial. At such cycle rates, however, the conduit connecting the valve to the load (diaphragm and cutter) may become very hot (e.g., hot enough to soften or melt the material of the conduit). Since this conduit typically includes a flexible plastic or rubber tube, the high temperature can soften the material, leading to changes in operating characteristics. The exhaust gas leaving the valve, in contrast, is colder.

SUMMARY

In accordance with one example construction, a heat exchange system for a surgical instrument includes a valve, a load, and a load conduit extending between the valve and the load. The load conduit delivers fluid from the valve to the load. The heat exchange system also includes an exhaust conduit that directs the fluid away from the valve. A portion of the load conduit is positioned so as to thermally transfer heat to a portion of the exhaust conduit.

In accordance with some constructions, the exhaust conduit includes an expansion chamber, and the portion of the load conduit is wrapped at least partially around the expansion chamber. In accordance with some constructions, the heat exchange system includes a manifold block, the exhaust conduit includes a channel in the manifold block, and the portion of the load conduit is positioned in the channel. In accordance with some constructions, the heat exchange system includes a manifold block, the exhaust conduit includes a chamber in the manifold block, and both the valve and a portion of the load conduit are disposed within the chamber.

Other embodiments and aspects of various embodiments will become apparent by consideration of the detailed description and accompanying drawings.

DETAILED DESCRIPTION

Before any embodiments are explained in detail, it is to be understood that the embodiments are not limited in their application to the details of construction and the arrangement of components set forth in the following description or illustrated in the following drawings. Other embodiments are possible and embodiments described and illustrated are capable of being practiced or of being carried out in various ways.

Figure 1:
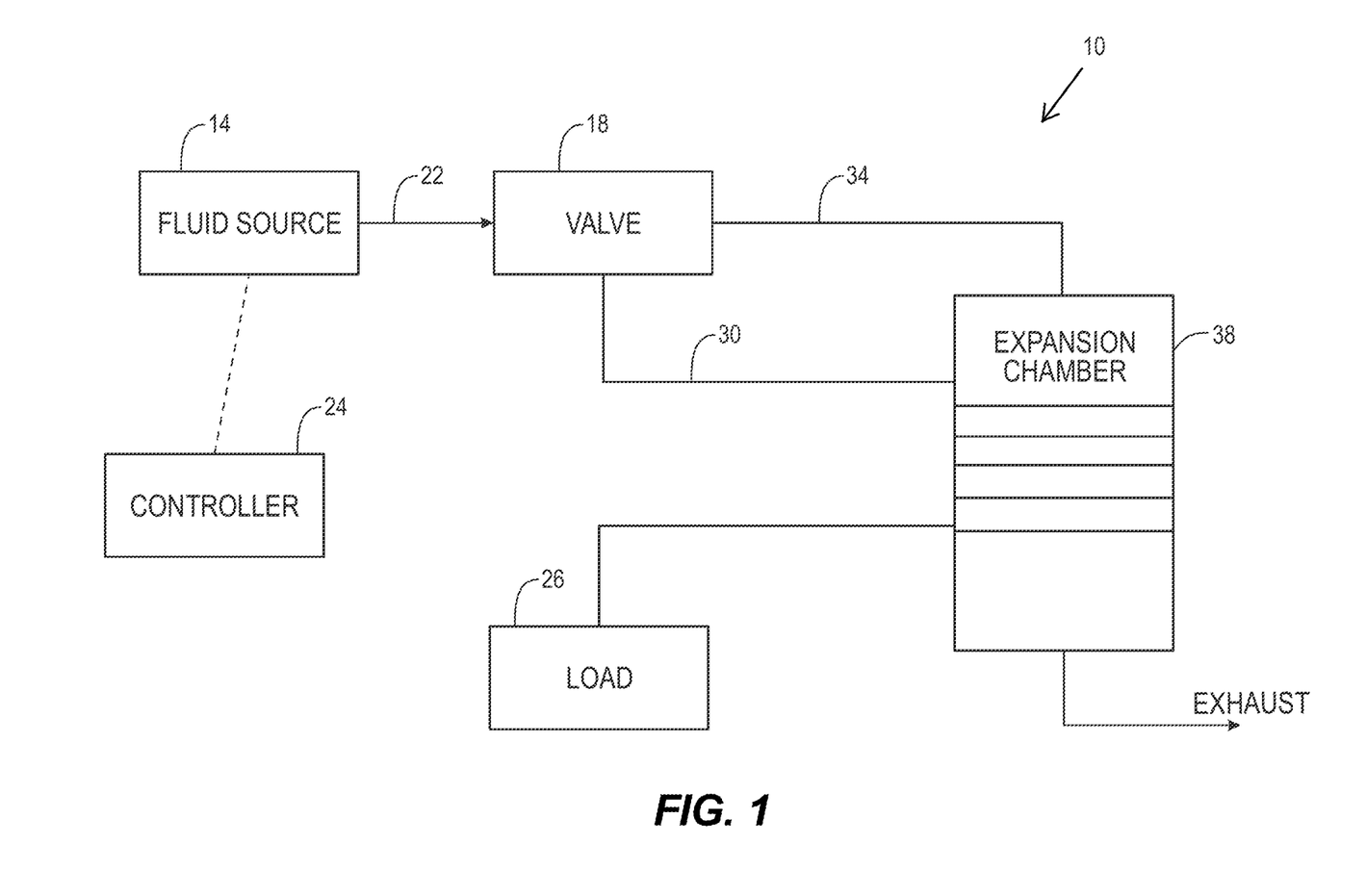
FIG. 1 schematically illustrates a heat exchange system for a pneumatically powered tool.
Figure 2:
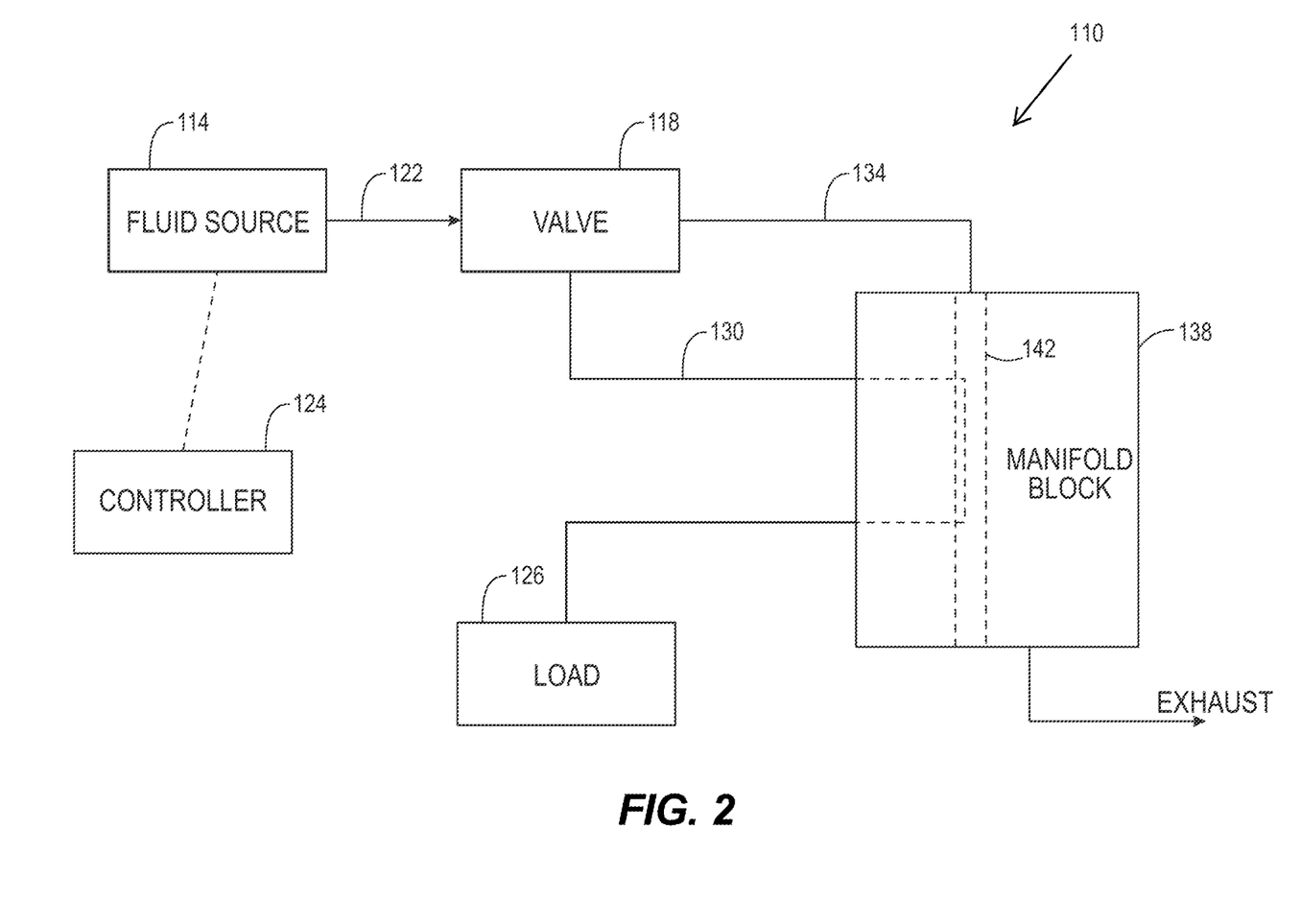
FIG. 2 schematically illustrates another heat exchange system for a pneumatically powered tool.
Figure 3:
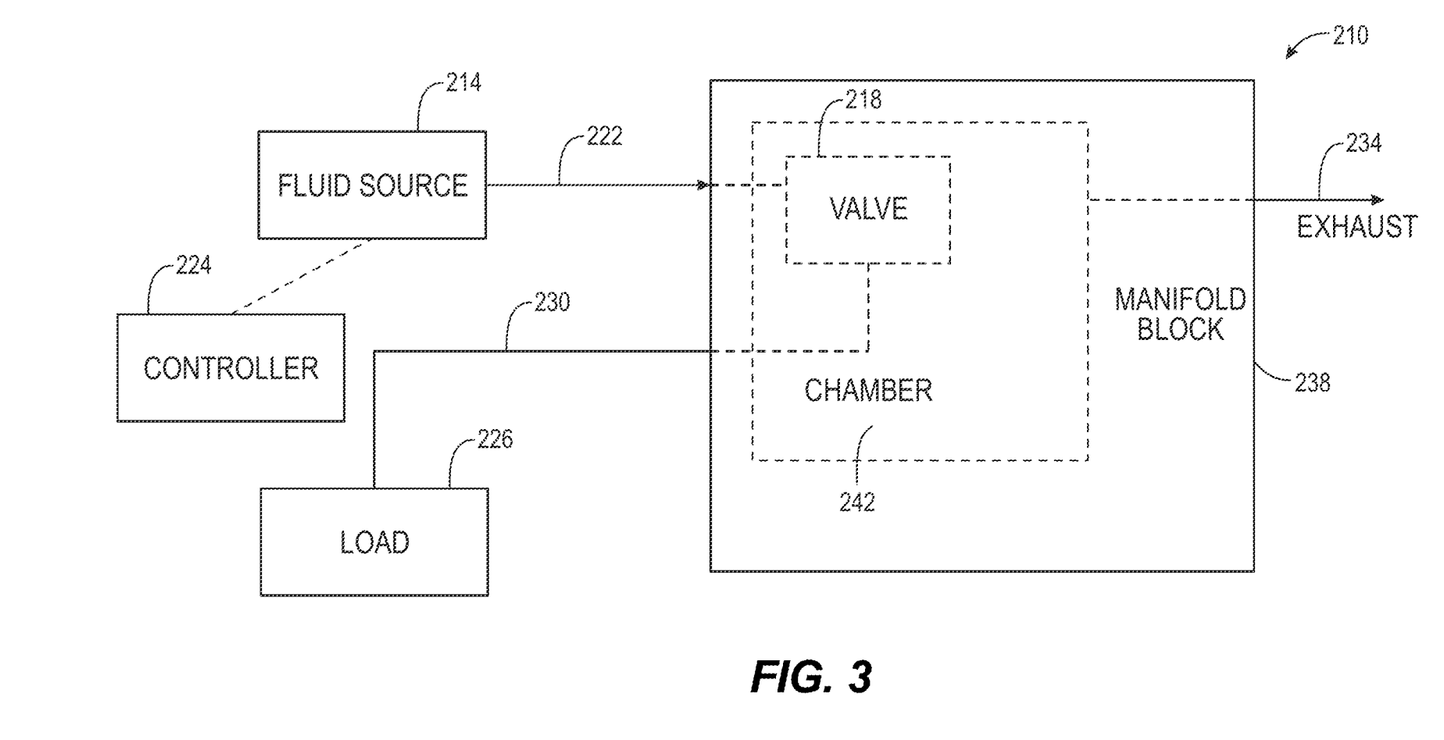
FIG. 3 schematically illustrates another heat exchange system for a pneumatically powered tool.

FIGS. 1-3 schematically illustrate various heat exchange systems for a pneumatically powered tool. Although certain examples of heat exchange systems are described in the context of being used with a vitreous cutting instrument, the heat exchange systems may be used with other powered tools, including other powered medical instruments.

With reference to FIG. 1, in one example construction, a heat exchange system 10 includes a fluid source 14. In the illustrated construction, the fluid source 14 is a source of compressed air, although other systems may use other types of fluids other than compressed air. The heat exchange system 10 also includes a valve 18 that is coupled to the fluid source 14 via a source conduit 22. The fluid source 14 delivers the compressed air through the source conduit 22 to the valve 18 (e.g., to an inlet port on the valve 18). In some constructions, the fluid source 14 is coupled to a controller 24 (e.g., through a wired connection or wireless connection) that regulates pressure in the fluid source 14, with the potential to adjust the source pressure dynamically to adapt to operating conditions.

The valve 18 may be a type of valve (e.g., poppet valve, sliding valve, rotating valve, etc.) that controls (e.g., regulates, or cycles) a flow of fluid. In some constructions, the valve 18 is controlled via a controller (e.g., the controller 24 or a different controller) that controls when the valve 18 moves (e.g., linearly or rotationally), to change the flow of fluid through the valve 18. As with the controller 24, in some constructions the controller for the valve 18 is coupled to the valve 18 via a wired or wireless connection. The valve 18 may include a number of openings, passageways, or other structures that facilitate a desired movement and flow of fluid through the valve 18. In some constructions, the controller 24 regulates pressure in the fluid source 14, with the potential to adjust the source pressure dynamically to adapt to operating conditions.

With continued reference to the example illustrated in FIG. 1, the heat exchange system 10 includes a load 26. In some instances, the load 26 is a structure that is driven (e.g., reciprocated) by a fluid (e.g., compressed air), such as a diaphragm of a vitreous cutting instrument, or another structure that is designed to receive the fluid and use the fluid to drive a powered tool. The load 26 is coupled to the valve 18 via a load conduit 30, such that at least a portion of the fluid that has been delivered to the valve 18 via the fluid source 14 is directed from the valve 18, through the load conduit 30, to the load 26. In some constructions, once the fluid has been used at or on the load 26, the fluid may return back through the same load conduit 30 to the valve 18, or may return for example through a separate conduit.

The heat exchange system 10 also includes an exhaust conduit 34 that exhausts fluid out of the heat exchange system 10 (e.g., exhausts the fluid that has been used at or on the load 26). In the illustrated construction, the exhaust conduit 34 exhausts the compressed air (e.g., used compressed air) from the valve 18 (e.g., out of an exhaust port on the valve 18), and through an expansion chamber 38 of the exhaust conduit 34. The expansion chamber 38 may be a manifold, or other structure, that includes one or more channels (e.g., conduits, chambers, or other openings or passageways) through which the exhausted compressed air passes and/or expands in volume as it travels away from the valve 18.

During times of high cycling (e.g., 200 cycles per second or more), the pressure of the fluid may increase within the load conduit 30. When the pressure of the fluid is increased, the temperature of the fluid may also increase. This causes the fluid in the load conduit 30 to have a higher temperature than the fluid supplied at the inlet port of the valve 18, and the fluid leaving the valve 18 at the exhaust port to have a lower temperature. These effects are small when the cycling rate is slow enough to allow heat to be conducted away. At high cycle rates, however, these effects can be pronounced. Accordingly, the load conduit 30 may become hot. Conversely, the fluid being exhausted away from the valve 18 via the exhaust conduit 34 may be significantly cooler, particularly within the expansion chamber 38 where the fluid may be expanding into a larger space.

Figure 4:
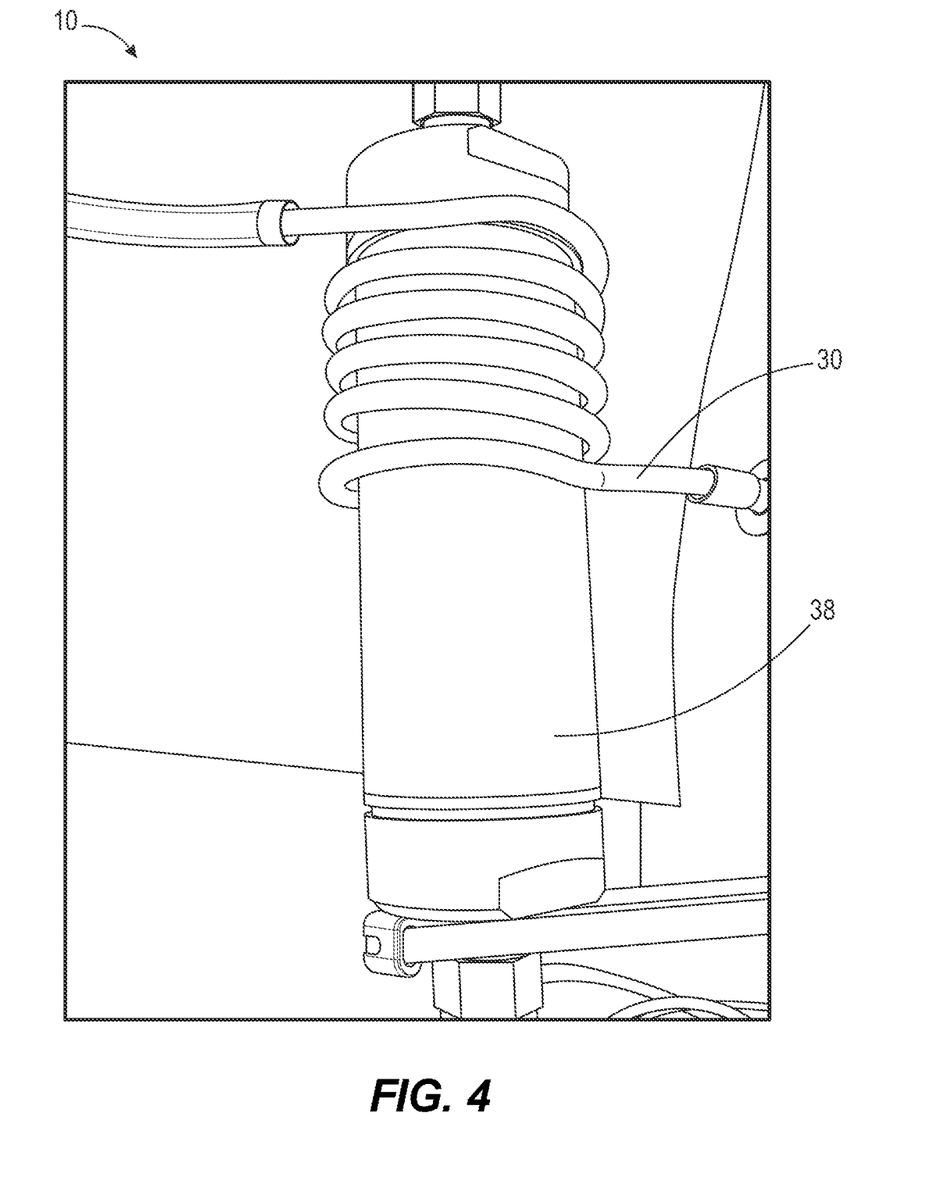
FIG. 4 is a perspective view of one example of a heat exchange system according to the schematic illustration in FIG. 1.

The heat exchange system 10 is therefore designed to facilitate thermal balance, and to reduce the likelihood of overheating of the load conduit 30, by directing at least a portion of the load conduit 30 around an exterior of the exhaust conduit 34 and transferring heat from the load conduit 30 (and from the hot fluid in the load conduit 30) to the exhaust conduit 34. For example, and with reference to FIG. 1 (as well as FIG. 4, illustrating an example of the heat exchange system 10 of FIG. 1), a portion of the load conduit 30 wraps, or coils, around the exterior of the expansion chamber 38 of the exhaust conduit 34. In some constructions the load conduit 30 may be in direct physical contact with an exterior surface of the expansion chamber 38. The number of coils, or wraps, around the expansion chamber 38 may vary and be different than that illustrated. For example, in some constructions, the load conduit 30 may only wrap a single time around the expansion chamber 38, or may wrap around or otherwise contact only a portion of the expansion chamber 38. Additionally, in some constructions, the load conduit 30 may additionally or alternatively wrap around or otherwise be in contact with another portion of the exhaust conduit 34, other than the expansion chamber 38.

In the illustrated construction, as hot compressed air travels through the load conduit 30, at least a portion of the heat is thermally transferred through the material of the load conduit 30, through the material of the expansion chamber 38, and to the cooler compressed air within the expansion chamber 38. The materials forming the load conduit 30 and the expansion chamber 38 may be selected, for example, based on thermal conductivity. For example, in some constructions the load conduit 30, the exhaust conduit 34, and/or the expansion chamber 38 are made partially or entirely of metal such as aluminum, or another highly thermally conductive material. The amount of heat that is exchanged, or the rate of heat that is exchanged, between the load conduit 30 and the exhaust conduit 34 may depend not only on the selected materials for the structures, but also for example upon the total number of coils, or the total contact surface area between the material of the load conduit 30 and the expansion chamber 38.

In some constructions, the exhaust conduit 34 specifically includes a metal expansion chamber 38. A portion of the load conduit 30, fabricated from, e.g., a metal tube, is wrapped around the expansion chamber 38 (e.g., wrapped at least once entirely around) to form a coil (see again FIGS. 1 and 4). The coiled load conduit 30 and the expansion chamber 38 are in direct physical contact, allowing transfer of heat from the hot metal load conduit 30 to the cold metal expansion chamber 38.

FIG. 2 schematically illustrates another construction in the form of a heat exchange system 110. The heat exchange system 110 includes a fluid source 114 and a valve 118. The valve 118 is coupled to the fluid source 114 via a source conduit 122. The fluid source 114 delivers the fluid (e.g., compressed air) through the source conduit 122 to the valve 118 (e.g., to an inlet port on the valve 118). In some constructions, the fluid source 114 is coupled to a controller 124 (e.g., through a wired connection or wireless connection) that regulates pressure in the fluid source 114, with the potential to adjust the source pressure dynamically to adapt to operating conditions. The valve 118 may also be controlled via a controller (e.g., the controller 124 or a different controller) that controls when the valve 118 should move (e.g., linearly or rotationally), to change the flow of fluid through the valve 118. As with the controller 124, in some constructions the controller for the valve 118 is coupled to the valve 118 via a wired or wireless connection. The valve 118 may include a number of openings, passageways, or other structures that facilitate a desired movement and flow of fluid through the valve 118.

The heat exchange system 110 also includes a load 126. Similar to the load 26, the load 126 may be a structure that is driven (e.g., reciprocated) by fluid, such as a diaphragm of a vitreous cutting instrument, or another structure that is designed to receive compressed gas and/or use the compressed gas to drive a powered tool. The load 126 is coupled to the valve 118 via a load conduit 130.

Figure 5:
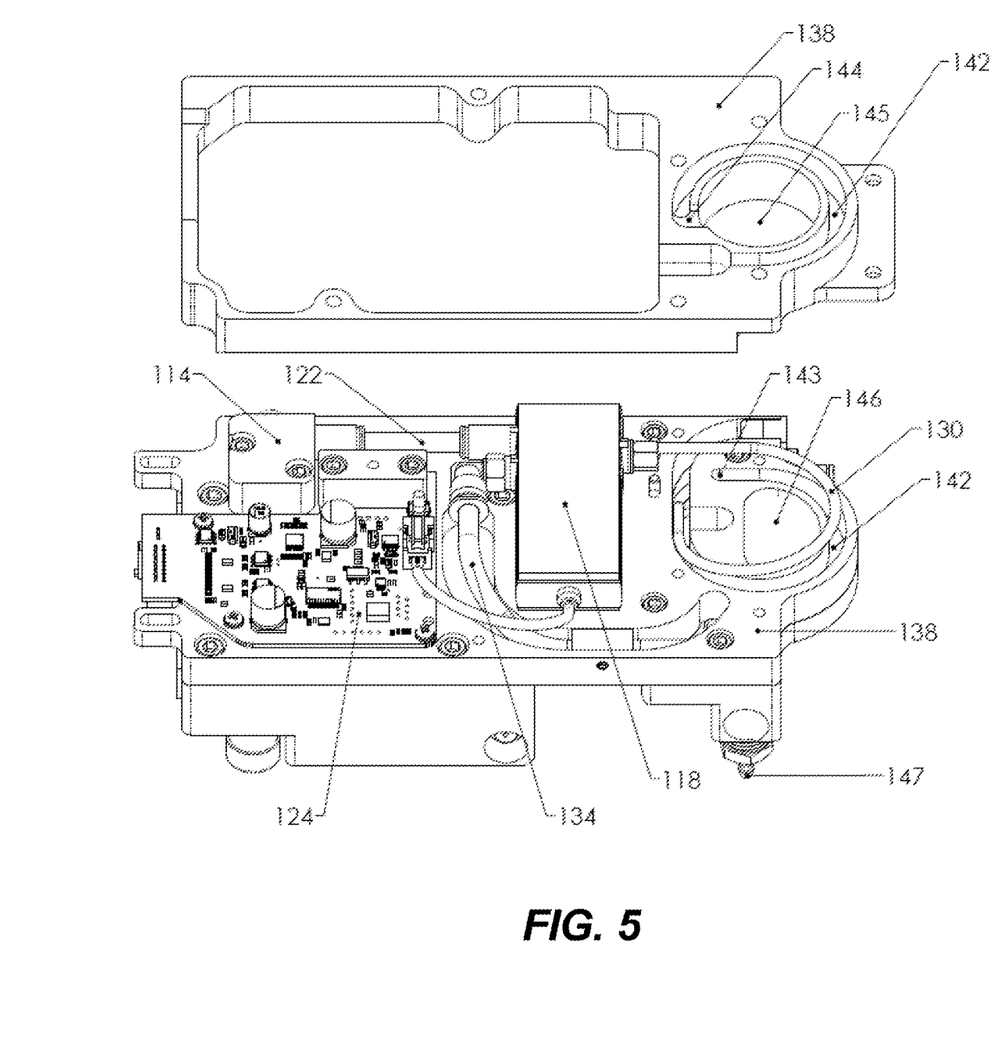
FIG. 5 is a perspective view of an example of a heat exchange system according to the schematic illustration in FIG. 2.

The heat exchange system 110 also includes an exhaust conduit 134 that exhausts fluid out of the heat exchange system 110 (e.g., exhausts the fluid that has been used at or on the load 126). In the illustrated construction, the exhaust conduit 134 exhausts compressed air (e.g., used compressed air) from the valve 118 (e.g., out of an exhaust port on the valve 118), and through a manifold block 138 (see also FIG. 5, illustrating an example of the heat exchange system 110 of FIG. 2). In some constructions the manifold block 138 may be formed from one or more housing elements (e.g., including a cover) coupled (e.g., fastened) together. (FIG. 5 shows the cover separated so as to illustrate the internal structures of manifold block 138.) Similar to the expansion chamber 38, the manifold block 138 may include, for example, one or more channels (e.g., conduits, chambers, or other openings or passageways) through which the exhausted compressed air may pass and/or expand in volume as it travels away from the valve 118. In some constructions, the manifold block 138 also includes one or more channels (e.g., chambers or other areas) within which a portion or all of the fluid source 114, the valve 118, the source conduit 122, and/or other structures are positioned or otherwise housed. In some constructions the load conduit 130, the exhaust conduit 134, and/or the manifold block 138 are made partially or entirely of metal such as aluminum, or another highly thermally conductive material.

In the example illustrated in FIG. 2, the manifold block 138 includes at least one channel 142 (e.g., elongate channel) through which exhausted fluid travels. The channel 142 effectively forms part of the exhaust conduit 134, and is sized and shaped to accommodate and receive a portion of the load conduit 130. For example, as illustrated in FIG. 2, the load conduit 130 passes out of the valve 118, and then enters into the manifold block 138 (e.g., through an opening along a side of the manifold block 138). A portion of the load conduit 130 then either passes through, or otherwise passes along or in close proximity to, the channel 142, so that the cooler exhausted fluid moving along the channel 142 directly contacts the outside surface of the load conduit 130. Through thermal transfer, the cooler fluid cools the hotter fluid traveling through the load conduit 130. The load conduit 130 then passes back out of the manifold block 138 to the load 126. As illustrated in FIG. 2, the channel 142 may extend entirely through the manifold block 138 (e.g., linearly). Other constructions include different shapes and sizes for the channel 142. In the example illustrated in FIG. 5, a portion of load conduit 130 is formed as a spiral and passes through a circular portion of channel 142. Exhaust conduit 134 directs exhaust gas into channel 142 at entry point 143. Gas flows through channel 142 in contact with load conduit 130 until reaching exit point 144. Gas flow then continues through expansion chamber 145 and muffler 146 before leaving manifold block 138 at vent 147.

In some constructions, the load conduit 130 winds or is directed in other directions and paths through the manifold block 138 other than those illustrated. In addition, in some constructions, the load conduit 130 comes in close proximity to more than one channel 142 in the manifold block 138 so as to be cooled by multiple channels. The channel 142 and the load conduit 130 both have a cross-sectional shape. For example, in some constructions, both the load conduit 130 and the channel 142 each have a semi-circular or circular cross-sectional shape, with the load conduit 130 having a smaller diameter than the channel 142 so that the load conduit 130 fits inside of and passes through the channel 142. Other constructions include different shapes and diameters.

In some constructions, the exhaust conduit 134 includes the channel 142 formed in the manifold block 138. A portion of the load conduit 130, fabricated specifically from a metal tube, is disposed inside of the channel 142. The cold exhaust gas is in direct contact with the hot metal load conduit 130.

FIG. 3 illustrates another example construction in the form of a heat exchange system 210. The heat exchange system 210 includes a fluid source 214 and a valve 218. Similar to the valves 18 and 118, the valve 218 is coupled to the fluid source 214 via a source conduit 222. The fluid source 214 delivers the fluid (e.g., compressed air) through the source conduit 222 to the valve 218 (e.g., to an inlet port on the valve 218). In some constructions, the fluid source 214 is coupled to a controller 224 (e.g., through a wired connection or wireless connection) that regulates pressure in the fluid source 214, with the potential to adjust the source pressure dynamically to adapt to operating conditions. The valve 218 may also be controlled via an electronic controller (e.g., the controller 224 or a different controller) that controls when the valve 218 moves (e.g., linearly or rotationally), to change the flow of fluid through the valve 218. As with the controller 224, in some constructions the controller for the valve 218 is coupled to the valve 218 via a wired or wireless connection. The valve 218 may include a number of openings, passageways, or other structures that facilitate a desired movement and flow of fluid through the valve 218.

The heat exchange system 210 also includes a load 226. Similar to the loads 26 and 126, the load 226 may be a structure that is driven (e.g., reciprocated) by fluid (e.g., compressed air), for example, a diaphragm of a vitreous cutting instrument, or another structure that is designed to receive fluid and/or use fluid to drive a powered tool. The load 226 is coupled to the valve 218 via a load conduit 230.

The heat exchange system 210 also includes an exhaust conduit 234 that exhausts (e.g., removes) fluid out of the heat exchange system 210. In the illustrated construction, the exhaust conduit 234 exhausts the fluid away from the valve 218, and out of a manifold block 238. Similar to the manifold block 138, the manifold block 238 may include, for example, one or more channels (e.g., conduits, chambers, or other openings or passageways) through which the exhausted fluid passes and/or expands in volume as it travels away from the valve 218. For example, in the illustrated construction, the manifold block 238 includes a chamber 242 that houses the valve 218, and also a portion of the source conduit 222. The chamber 242 is larger than the valve 218, so that when the compressed air is exhausted out of the valve 218 (e.g., out of an outlet port on the valve 218), the exhausted air enters (e.g., immediately enters) the chamber 242, before then passing through the exhaust conduit 234. In this construction, the chamber 242 therefore effectively becomes a portion of the exhaust conduit 234 itself. To facilitate thermal transfer, the load conduit 230, the exhaust conduit 234, and/or the manifold block 238 may be made partially or entirely of metal or another highly thermally conductive material.

With continued reference to FIG. 3, in the illustrated construction a portion of the load conduit 230 extends from the valve 218 and through a portion of the chamber 242, before passing out of the manifold block 238 to the load 226. Through thermal transfer, the colder fluid (e.g., compressed air) in the chamber 242 cools this portion of the load conduit 230, and the hot fluid in the load conduit 230. In some constructions, the portion of the load conduit 230 that is disposed inside the manifold block 238 may be partially or entirely positioned within a separate channel or chamber that is in communication with the chamber 242, so that cooler fluid may flow between the chamber 242 and the separate channel or chamber, facilitating a cooling of the load conduit 230.

In some constructions, the chamber is 242 is formed in the manifold block 238. The chamber 242 is in communication with the channel in which the load conduit 230 is disposed. The valve 218 is disposed inside of the chamber 242, with conduits passing into the chamber 242 to bring compressed gas to the pressure port of the valve 218 and passing out of the chamber 242 to connect to the load 226. The exhaust port of the valve 218 empties directly into the chamber 242, so that the chamber 242 is a portion of the exhaust conduit 234.

Other constructions of the heat exchange systems described herein may include arrangements of channels (e.g., chambers, and/or other openings) that differ from those illustrated for the expansion chamber 38 and the manifold blocks 138, 238. Other constructions of the heat exchange systems may also include numbers and arrangements of load and exhaust conduits that differ from those illustrated. For example, in some constructions, the heat exchange systems 10, 110, or 210 include two or more load conduits, rather than one, that extend between the valve 18, 118, or 218 and the load 26, 126, or 226, to separately deliver compressed gas from the valve 18, 118, or 218 to two different areas in the powered tool (e.g., to opposite sides of a diaphragm). Additionally, in some constructions the heat exchange systems include two or more exhaust conduits, or two or more expansion chambers or manifold blocks. In some constructions, the heat exchange systems use both an expansion chamber and a manifold block.

Additionally, in some constructions, in order to efficiently transmit pneumatic pressure pulses to the load 26, 126, 226, the load conduit 30, 130, 230 (e.g., metal tube or other thermally conductive material) is designed to minimize changes in cross section along its length. In some constructions the load conduit 30, 130, 230 has several portions fabricated from different materials (typically including a section of flexible material) but an effort is generally made to keep approximately (but not necessarily exactly) the same cross section in all portions. In some constructions, most portions of the load conduit 30, 130, 230 are tubular in form. In contrast, in some constructions the exhaust conduit 34, 134, 234 does not maintain a constant cross section. Changes in cross section, such as expansion chambers, for example may be beneficial to the performance of the system.

As described above, the heat exchange systems provide a means to transfer heat from a hot load conduit 30, 130, 230 to a cold exhaust gas, thereby reducing and stabilizing the temperature of the load conduit 30, 130, 230. The heat exchange systems may take several forms, such as those illustrated in FIGS. 1-5, and may include combinations of elements from one or more of these systems. In at least some of the forms, some portion of the load conduit 30, 130, 230 (e.g., fabricated from a thermally conductive material) is brought into contact with the cold exhaust gas, either directly or indirectly. A portion of the load conduit 30, 130, 230 is positioned so as to thermally transfer heat to a portion of the exhaust conduit 34, 134, 234.

In order to efficiently transmit pneumatic pressure pulses to the load 26, 126, 226, and as described above, the load conduit 30, 130, 230 may minimize changes in cross section along its length. The load conduit 30, 130, 230 may have several portions fabricated from different materials (e.g., typically including a section of flexible material) and the load conduit 30, 130, 230 may have approximately (but not necessarily exactly) the same cross section in all portions. Although embodiments have been described in detail with reference to certain preferred embodiments, variations and modifications exist within the scope and spirit of the subject matter described.

What is claimed is:

1. A heat exchange system for a surgical instrument, the heat exchange system comprising:
   a valve;
   a load;
   a load conduit extending between the valve and the load, and configured to deliver fluid from the valve to the load;
   an exhaust conduit configured to direct the fluid away from the valve; and
   a manifold block, wherein a portion of the exhaust conduit includes a channel in the manifold block, wherein the exhaust conduit extends from the valve, enters and passes through the manifold block, and extends away from the manifold block, and wherein a portion of the load conduit is positioned in the channel so as to thermally transfer heat to a portion of the exhaust conduit.

2. The heat exchange system of claim 1, further comprising a fluid source coupled to the valve.

3. The heat exchange system of claim 2, wherein the fluid source is a source of compressed gas.

4. The heat exchange system of claim 2, further comprising a controller coupled to the fluid source.

5. The heat exchange system of claim 1, further comprising a controller coupled to the valve.

6. The heat exchange system of claim 1, wherein the load is a diaphragm of a vitreous cutting instrument.

7. The heat exchange system of claim 1, wherein the load conduit extends from the valve, enters the manifold block, passes into the channel in the manifold block, extends away from the channel and the manifold block, and extends to the load.

8. The heat exchange system of claim 7, wherein the load conduit enters the manifold block through an opening along a side of the manifold block.

9. The heat exchange system of claim 1, wherein the load conduit is made at least partially of metal.

10. The heat exchange system of claim 1, wherein the exhaust conduit is made at least partially of metal.

11. The heat exchange system of claim 1, wherein the channel in the manifold block includes a chamber wherein both the valve and the portion of the load conduit are disposed within the chamber, and wherein the exhaust conduit extends from the chamber, and extends out of the manifold block so as to remove the fluid from the chamber.

12. The heat exchange system of claim 11, wherein the exhaust conduit is arranged such that the fluid exiting the load is configured to only be directed out of the manifold block, and not into the manifold block.

13. The heat exchange system of claim 11, further comprising a fluid source coupled to the valve, wherein the fluid source is a source of compressed gas.

14. The heat exchange system of claim 11, wherein the load is a diaphragm of a vitreous cutting instrument.

* * * * *